United States Patent
Maevsky et al.

(10) Patent No.: US 6,562,872 B1
(45) Date of Patent: May 13, 2003

(54) EMULSION OF PERFLUOROORGANIC COMPOUNDS FOR MEDICAL PURPOSES, A PROCESS FOR THE PREPARATION THEREOF AND METHODS FOR TREATING AND PREVENTING DISEASES WITH THE USE THEREOF

(75) Inventors: Evgeny Iliich Maevsky, Puschino (RU); Genrikh Romanovich Ivanitsky, Puschino (RU); Kirill Nikolaevich Makarov, Moscow (RU); Galina Mikhailovna Kulakova, Puschino (RU); Vladimir Viktorovich Arkhipov, Puschino (RU); Viktor Vasilievich Moroz, Moscow (RU); Ljudmila Nikolaevna Starovoitova, Puschino (RU); Raisa Yakovlevna Senina, Puschino (RU); Sergei Jurievich Pushkin, Noginsk (RU); Albina Ivanovna Ivashina, Moscow (RU)

(73) Assignee: Otkrytoe Aktsionernoe Obschestvo Naucho-Proizvodstven-Naya Firma "Perftoran", Puschino Moskovskaya oblast (RU)

( * ) Notice: Subject to any disclaimer, the term of this patent is extended or adjusted under 35 U.S.C. 154(b) by 0 days.

(21) Appl. No.: 09/830,563
(22) PCT Filed: Jul. 20, 2000
(86) PCT No.: PCT/RU00/00309
§ 371 (c)(1), (2), (4) Date: May 7, 2001
(87) PCT Pub. No.: WO02/07717
PCT Pub. Date: Jan. 31, 2002

(51) Int. Cl.⁷ .................. A61K 31/02; A61K 31/025; A61K 31/13; A61K 9/107; B01F 17/42
(52) U.S. Cl. .................. 514/672; 514/757; 514/824; 514/832; 514/833; 516/76; 516/929
(58) Field of Search .................. 516/76, 929; 514/672, 514/757, 832, 833, 824

(56) References Cited

U.S. PATENT DOCUMENTS

| | | | |
|---|---|---|---|
| 3,778,381 A | * 12/1973 | Rosano et al. | 516/76 X |
| 4,369,127 A | * 1/1983 | Cormier et al. | 516/76 X |
| 4,775,522 A | * 10/1988 | Clark, Jr. | |
| 4,859,363 A | 8/1989 | Davis et al. | 514/832 X |
| 4,866,096 A | * 9/1989 | Schweighardt | 514/756 |
| 5,374,624 A | * 12/1994 | Segel | 514/756 X |
| 5,403,575 A | * 4/1995 | Kaufman et al. | 514/757 X |
| 5,674,913 A | * 10/1997 | Clark, Jr. | 514/755 |
| 5,914,352 A | 6/1999 | Weers et al. | 514/757 |
| 6,113,919 A | * 9/2000 | Reiss et al. | 516/76 X |
| 6,315,756 B1 | * 11/2001 | Tankovich | 514/672 X |

FOREIGN PATENT DOCUMENTS

| | | |
|---|---|---|
| EP | 0 307 087 | 3/1989 |
| RU | 797546 | 1/1981 |
| RU | 2070033 | 12/1996 |
| RU | 2088217 | 8/1997 |
| RU | 2107496 | 3/1998 |
| RU | 2122404 | 11/1998 |
| RU | 2144817 | 1/2000 |
| WO | WO 95/33447 | 12/1995 |

OTHER PUBLICATIONS

G.R. Ivanitskii, et al., Perfluorocarbon Active Media for Medicine and Biology (New Aspects of Research), pp. 5–33, "Engineering of Artifical Blood Plasma Subsititutes with Gas Transport Function on the Basis of Perfluorocarbon Emulsions", 1993 (with English translation of p. 27).

K. Vaichulis, et al., Physiological Activity of Flurine–Containing Compounds (Experiment and Clinical Practice), pp. 213–216, "Use of Perftoran in Intensive Therapy of Alcholic Psyschosis", 1995 (with English translation).

Editor–in–chief V.I. Pokrovskii, small Medical Encyclopedia, Meditsina Publishers, vol. 6, pp. 259–360, 1996.

A. N. Sklifas, et al., Perfluorocarbon Active Media for Medicine and Biology (New Aspects of Research) pp. 128–135, "Investigation of Toxicity Mechanism of perfluorodecalin Emulsion for Rabbits", 1993( with partial English translation).

A. M. Golubev, Perfluorocarbon Active Media for Medicine and Biology (New Aspects of Research), pp. 88–93, "Results and Prospects of Studying the Effects of Fluorocarbon Blood Substitutes on Biological Systems", 1993(with partial English translation).

L. E. McCoy, et al., Scanning Electron Microscopy, pp. 311–319, "Endothelial Response to Perfluorochemical Perfusion", 1984.

* cited by examiner

Primary Examiner—Richard D. Lovering
(74) Attorney, Agent, or Firm—Oblon, Spivak, McClelland, Maier & Neustadt, P.C.

(57) ABSTRACT

An emulsion of perfluoroorganic compounds (PFOC) comprises a rapidly eliminable perfluorocarbon (PFC) and a slowly eliminable perfluorinated cyclic tertiary amine, perfluoro-N-4-(methylcyclohexyl)-piperidine and additionally comprises not less then three rapidly eliminable and three slowly eliminable PFOC admixtures with the critical temperature of dissolution in hexane (CTDH) close to that of main PFOC. The PFOC emulsion is stabilized with a polyoxyethylene-polyoxypropylene copolymer having low viscosity to provide high dynamic oxygen capacity and enhancing oxygen delivery to tissues. To prepare the emulsion the stabilizing agent is heated up to 75° C., all components are saturated with carbon dioxide gas to minimize the reactogenicity in intravessel injection as a means of compensation for mass blood loses, perfusion of organs cut of blood flow, treating air-and fat embolism, obliterating vascular injuries of extremities and preventing toxic injuries caused by various xenobiotics.

54 Claims, 2 Drawing Sheets

EMULSION OF PERFLUOROORGANIC COMPOUNDS FOR MEDICAL PURPOSES, A PROCESS FOR THE PREPARATION THEREOF AND METHODS FOR TREATING AND PREVENTING DISEASES WITH THE USE THEREOF

This application is a national-stage filing under 35 U.S.C. §371 of PCT/RU00/00309, filed Jul. 20, 2000.

TECHNICAL FIELD

The present invention relates to the field of medical industry and is concerned with a composition of and a process for the preparation of a medicinal form of emulsions of perfluoroorganic compounds (PFOC) with gas-transporting properties, intended, in particular, for intravenous administration when compensating for blood losses and for treating various diseases accompanied by hypoxic or ischemic lesions, and also as contrast and perfusion media.

STATE OF THE ART

Though the range of possible applications of gas-transporting PFOC emulsions keeps on extending, on the whole the application of these preparations is still limited in view of the following factors.

The delivery of oxygen is not sufficiently effective, particularly because of insufficient oxygen capacity of PFOC emulsions compared with whole blood, which makes those engaged in developing PFOC emulsions increase the concentration of gas-transporting components, for example, up to 65 vol. % [European Patent No. 0307087B1, publication dated 08.06.1994]. However, an increase of the PFOC concentration in the emulsion is inevitably accompanied by a sharp increase in the viscosity of the preparations. As a result, emulsions with a high PFOC concentration, in spite of a high absolute oxygen capacity, do not provide sufficiently effective oxygen delivery to the tissues due to the small dynamic oxygen capacity determined by the absolute oxygen capacity/viscosity ratio. When the viscosity of the preparation is high, the compensatory reactions of the cardiovascular system, directed to increasing the minute volume and raising the rheological properties of blood, can provide neither sufficient perfusion of large vessels nor effective circulation, and, consequently, the delivery of oxygen to the tissues is disturbed.

The reactogenicity of PFOC emulsions is relatively high. The reactogenicity is associated, in the first place, with the formation of peroxide radicals in the stabilizing agent [L. E. McCoy, C. A. Berker, T. H. Goodin, M. J. Barnhart, //Scann. Electron. Microscopy, 1984, v. 1, p. 311] which forms an adsorption layer of the PFOC particles, and, in the second place, with the presence of large particles in the emulsion, which are recognized by the immune system of the organism as foreign agents [S. I. Vorob'ev et al., "Comparative study of some perfluorocarbon emulsions", in: Physiological Activity of Fluorine-containing Compounds (Experiment and Clinic), Pushchino, 1995, pp. 33–41 (in Russian)].

The possibility of manifestation of toxicity of the emulsions, caused by the effect of lipophilic perfluorocarbons rapidly eliminable from the organism, traditionally used for producing gas-transporting blood substitutes, on biological structures, and by possible aggregation and coarsening of emulsion grains in the blood flow. Rapidly eliminable perfluorocarbons easily interact with enzymatic systems and biological membranes, formed elements and proteins of blood, and, as is shown by a number of investigations, Induce an anaphilactogenic reaction and delayed death (in 50–80 days) of large laboratory animals having a low blood flow rate, comparable with that in humans (A. N. Sklifas, V. V. Obraztsov, K. N. Makarov, D. G. Shekhtman, N. I. Kukushkin, "Investigation of the Toxicity Mechanism of Perfluorodecalin Emulsion for Rabbits", in collected articles: "Perfluorocarbon Active Media for Medicine and Biology. New Aspects of Research". Pushchino, 1993, pp. 129–135 (in Russian)].

High cost of PFOC emulsion preparations, associated with the necessity of preparing individual PFOCs and high requirements to their purification from admixtures, which makes them difficult of access for users.

Binary PFOC emulsions are known (see, e.g., USSR Patent No. 797546, publ. in Bull. "Otkrytiya, Izobreteniya, . . . ", No. 2, 15.01.1981, or RF Patent No. 2088217, publ. in Bull. "Izo-breteniya . . . (Zayavki . . . ,)", No. 24, 27.08.1997), in which, for lowering the toxicity, in addition to rapidly eliminable perfluorocarbons, slowly eliminable substances are contained, for instance, perfluorinated tertiary amines, which possess expressed lipophobic properties and do not interact in any manner with biological objects. For example, it has been shown that the presence in the composition of the emulsions and even long-term acctmulation in organs of slowly eliminable perfluorotributylamine, which is retained in macrophages of different organs for a period commensurable with the life time of animals (and which is therefore not used for medical purposes) does not bring about any pathological changes. This is confirmed by more than 30 years of investigations aimed at finding toxicity and probable cancerogenicity and by 16 years of experience in medical uses of emulsions of perfluoroorganic compounds, containing other relatively slowly eliminable perfluorinated tertiary amines [Biomaterials, artificial cells, and artificial organs. 1988, vol. 16, No. 1–3, Special Issue from III International Symposium on "Blood Substitutes"; A. M. Golubev, Advances in and Prospects of Studying the Influence of Fluorocarbon Blood Substitutes on Biological Systems./Perfluorocarbon Active Media for Medicine and Biology (New Aspects of Research). Pushchino: ONTI of Pushchino Research Center, Russian Academy of Sciences, 1993, pp. 88–93 (in Russian)].

The binary PFOC emulsion according to RF Patent No. 2088217 is the closest to the claimed emulsion with regard to the formulation of its components. It comprises a mixture of a rapidly eliminable lipophilic perfluorocarbon perfluorodecalin (PFD) or perfluorooctylbromide and a slowly eliminable lipophobic perfluorinated tertiary amine perfluoro-N-(4-methylcyclohexyl)-piperidine (PFMCP) in a ratio of 40–50 vol. % to 1–10 vol. %, and is stabilized by phospholipids the amount of which is from 2 to 6%. Upon intravenous administration of such emulsion, 100% of rabbits survive during 60 days of observations. However, this emulsion has a high viscosity (14–16 cP), which, as indicated above, in spite of the high absolute oxygen capacity of the preparation, leads to a sharp drop of the dynamic oxygen capacity and does not provide efficient delivery of oxygen.

Furthermore, the use of such sharply differing in their physical properties PFOC as the lipophilic PFD and lipophobic PFMCP leads to clustering of the fluorocarbon phase inside the emulsion particles, which complicates the choice of the stabilizing agent and impairs the emulsion stability. As a result, the emulsion dispersity changes both during storage and when the emulsion enters the blood flow.

Finally, in this invention individual highly purified perfluorodecalin and perfluoro-N-(4-methycyclohexyl)- piperidine are used for preparing the emulsion, which, as already indicated, makes the PFOC emulsion appreciably more expensive.

A PFOC emulsion is known, which is closest to the claimed one in the composition and in the ratio of the components [see RF Patent No. 2070033, publ. in Bull. "Izbreteniya . . . (Zayavki, . . . )", No. 34, 27.08.97]. This emulsion contains perfluorocarbon in the form of cis- and trans-isomers of perfluorodecalin and perfluorinated tertiary amine perfluoro-N-(4-methylcyclohexyl)-piperidine in lower concentrations of both components: 7 vol. % and 3.5 vol. %, respectively, and it is stabilized by a polyoxyethylene-polyoxypropylene copolymer with a molecular mass of 6–8 thousand Dalton (Da) with a mean size of emulsion particles of 0.08–0.1 $\mu$m. This composition, with a comparatively small value of the absolute oxygen capacity (7 vol. % of oxygen at $pO_2$ of 760 mm Hg), ensures owing to its small viscosity (3.5 cP) a higher dynamic oxygen capacity than other known PFOC emulsions (see Table 1 in the specification to said RF Patent), i.e., it ensures better oxygen delivery to the tissues. Owing to the high proportion of the slowly eliminable PFMCP (the PFMCP/PFD ratio=1:2) in the PFOC formulation and the high degree of monodispersity of the particles along with their size, this emulsion is not toxic for large animals. However, the emulsion according to RF Patent No. 2070033 is not free from a number of disadvantages: a relatively high reactogenicity because of formation of peroxide compounds in the stabilizing agent in the process of manufacture and during storage of the emulsion; insufficient stability upon repeated freezing-defrosting the emulsion, when the emulsion enters the blood flow, and when it gets in contact with high-molecular dextrans, since two PFOC sharply differing in their physicochemical properties are used in the composition of the emulsion; and a high cost of the preparation due to the use of highly purified PFD and PFMCP.

Known in the art is a process for the preparation of PFOC emulsions for medical purposes, in which process for reactogenicity it is proposed to decrease the mean size and to increase the monodispersity of the emulsion particles (see the specification to RF Patent No. 2070033). These properties are secured by adding dropwise a mixture of two forms of liquid PFOC to an aqueous solution of a stabilizing agent, thereby precluding the origination of a macroscopic interface, increasing the contact time and area of the PFOC with the stabilizing agent in the step of preparing the pro-emulsion. A submicron emulsion is prepared in a two-circuit homogenization system in the process of 12-fold recirculation in the homogenizer circuits. According to the specification of the cited invention, the first and second circuits of the homogenizer are used alternately, the homogenization process being thus slowed down, because returning from the second circuit to the first circuit leads to coarse pro-emulsion particles and even drops of PFOC, which are inevitably formed and retained on the walls of the chamber and pipes in the first circuit, getting into the already finely divided fine-dispersed emulsion. Furthermore, as it was already mentioned when criticizing the formulation of the emulsion, this process does not prevent formation of peroxide compounds.

DISCLOSURE OF THE INVENTION

It is an object of the proposed invention to provide such a composition of a PFOC emulsion, which ensures a reduction of the reactogenicity of the preparation and of the toxicity thereof for large animals and humans, a high dynamic oxygen capacity, a high stability on repeated freezing-defrosting and on contact with high-molecular dextrans used as blood substitutes.

Another object of the proposed invention is to develop such a process for the preparation of a pro-emulsion and a submicron emulsion proper, which, while preserving a high monodispersity of the system and with a prescribed small size of particles, inhibits the formation of peroxide compounds in the course of preparing the emulsion and during storage thereof.

Still another object of the invention is to reduce the capital inputs, to simplify and speed-up the process of preparing the PFOC emulsion, this being necessary for the industrial-scale manufacture of the drug.

The first object of the present invention is accomplished by that the known PFOC emulsion for medical purposes, which comprices a rapidly eliminable perfluorocarbon and a slowly eliminable perfluorinated tertiary amine, a stabilizing agent and a physiologically acceptable aqueous-saline solution with an energy-metabolism substrate, according to the invention, further comprises admixtures of at least three rapidly eliminable cis- and trans-isomers of perfluorocarbons $C_7$–$C_{10}$ and of at least three slowly eliminable perfluorinated tertiary amines $C_{11}$–$C_{13}$, close in physicochemical properties to the main perfluoroorganic compounds, for instance, in the critical temperature of dissolution in hexane, and minor admixtures of H-perfluoroalkanes. The content of the admixtures of rapidly eliminable perfluorocarbons does not exceed 15% of the content of the main perfluorocarbon; the content of the admixtures of slowly eliminable perfluorinated tertiary amines does not exceed 50% of the content of the main perfluorinated tertiary amine; and the content of admixtures of H-perfluoroalkanes does not exceed 0.1 vol. %. A the rapidly eliminable perfluorocarbon a mixture of cis- and trans-isomers of perfluorodecalin or perfluorooctyl bromide is used, and as the slowly eliminable PFOC perflluoro-N-4-(methylcyclohexyl)-piperidine is used. As the stabilizing agent a polyoxyethylene-polyoxypropylene copolymer with the molecular mass of 6–10 thousand Da is used.

The ratio of the perfluorocarbons and perfluorinated tertiary amires is 2:1 or 3:1.

In the preferable embodiment the emulsion comprises the main rapidly eliminable perfluorocarbon in the form of cis- and trans-isomers of perfluorodecalin in an amount of 6 vol. % and admixtures of rapidly eliminable perflufluorocarbons $C_7$–$C_{10}$ comprising a mixture of perflufluoromethylindane, perfluoro-1-methyl-3-propylcyclohexane, trans-perfluoroindane, perfluoro-4-oxodecalin, perfluorobutylcyclohexane, perfluoropropylcyclohexane, perfluoroethylcyclohexane, perfluorobutylcyclopentane, cis-perfluoro-1-methyl-2-ethylcyclohexane in a total amount of 0.7 vol. %; the main slowly eliminable perfluorinated tertiary amine perfluoro-N-4-(methylcyclohexyl)-piperidine in the form of a mixture of isomers in an amount of 2.3 vol. % and an admixture of slowly eliminable perfluorinated tertiary amines $C_{11}$–$C_{13}$ comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, isomers of perfluoromethylpropyl-(methylcyclopentyl)-amine and perfluoro-N-(4-methylcyclohexyl)-1-methylpiperidine in a total amount of 1.0 vol. %; and also admixtures of H-perfluoroalkanes in an amount of 0.02 vol. %.

In the preferred embodiment the ratio of the rapidly and slowly eliminable PEOC is 2:1. The content of the polyoxyethylene-polyoxypropylene copolymer with a molecular mass of 8 thousand Da is 4%, with the ratio of the polyoxyethylene and polyoxypropylene blocks in the copolymer being 4:1.

When the PFOC emulsion is used as a plasma substitute and for the perfusion of organs, the physiologically acceptable aqueous-saline solution contains 102 mM of NaCl, 5.2 mM of KCl, 1.8 mM of $MgCl_2$, 7.7 mM $NaHCO_3$, 1.65 mM of $NaH_2PO_4$ and 11 mM of D-glucose.

When the emulsion is used for the anti-ischemic protection of the heart disconnected from the blood flow in the course of pharmaco-ice-chip cardioplegia, the aqueous-saline solution contains 102 mM of NaCl, 5.2 mM of KCl, 1.8 mM of $MgCl_2$, 7.7 mM $NaHCO_3$, 1.65 mM of $NaH_2PO_4$ and 11 mM of D-glucose, 5 mM of sodium pyruvate, 5 mM of sodium β-oxybutyrate, 5 mM of sodium succinate, 5 mM of sodium glutamate, 5 mM of taurine.

Such content and composition of perfluorocarbons and perfluorinated tertiary amines corresponds to the composition of underrefined PFD and PFMCP which practically do not display any toxic properties either per se (in tests on isolated cultivated lymphoid cells) or in the formulation of the emulsion (in tests on small rodents and rodents), similarly to individual highly purified PFD and PFMCP containing no admixtures of other PFOC (Tables 1 and 2). This should be accounted by that the toxicity of PFOC stems not from their form, but from the presence of underfluorinated admixtures. If the latter are absent, then the next factors responsible for the toxicity are the concentration of fluorine in the aqueous phase, the detergent properties of the stabilizing agent, the appearance of peroxides and the presence of coarse or easily coalescing particles in the emulsion. Death of large animals, e.g., of rabbits, can be caused, as it follows from the data presented in Table 3 of the specification to RF Patent 2088217, by the use in the composition of the emulsion of exclusively rapidly eliminable highly lipophilic perfluoroorganic compounds, whereas introducing a lipophobic, i.e., a slowly eliminable PFMCP component, leads to a decrease in the toxicity, as a result of which the survival of rabbits reaches 100% during 60 days after administering 20 ml of the PFOC emulsion per kg of the body weight. A comparison of PFOC emulsions in terms of this parameter shows (Table 2) that the composition being patented by us does not cause death of rabbits even after 20-fold administration of the indicated dose. More than that, if the composition being patented is administered prior to, simultaneously with, or at least a weak after the administration of an emulsion manufactured only from PFD (ensuring 100% death of rabbits), all the animals survive (Table 2).

Impurity PFOCs present in the formulation of the emulsion have a structure close to the structure of the main PFOCs and constitute a number of PFOCs with gradually changing lipophilic-lipophobic properties (FIG. 1, Table 3). This contributes to the formation of a more homogeneous not clustered fluorocarbon phase inside the emulsion particles, increases the stability of the emulsion particles, decreases the intramolecular distillation phenomena responsible for coarsening of the particles, inhibits the aggregation of the particles both when they enter the blood flow and upon repeated freezing and upon contact with high-molecular oncotic agents of dextran nature (Table 4).

The presence in the fluorocarbon phase of a set of PFOCs with manifest lipophobic properties, particularly of perfluorinated tertiary amines displaced to the surface of the fluorocarbon; phase, contributes to better interaction with the stabilizing agent, i.e., with a polyoxyethylene-polyoxypropylene block copolymer, and to retaining it in the adsorption layer. As a result, the surface of the emulsion particles becomes less loose, acquires improved rheological characteristics: a lower viscosity and, as a consequence, a higher dynamic oxygen capacity at the same value of the absolute oxygen capacity, as well as an increased stability both in vitro (Table 4) and in the blood flow, which manifests itself in an increased time of the emulsion circulation (Table 5).

In the known literature sources no description can be found of PFOC emulsions comprising a mixture of several PFOC in structure, which differ in the physicochemical parameters so that they constitute a series of compounds with the properties gradually changing from lipophilic to lipophilic ones.

In FRG laid-open Application No. 4325100 A1 a PFOC emulsion is described, containing admixtures of H-perfluoroalkanes in an amount of 1 to 5%. The authors of said Application believe that this makes it possible to improve the oxygen-transporting properties of the emulsion and to lower its cost by reducing expenditures for the PFOC purification. However, an analysis carried out by us has shown that the content of H-perfluoroalkanes higher than 1 wt. % (0.5 vol. %) can lead to the appearance of toxicity in the preparations of emulsions both for isolated cultivated cells and for an integral organism.

The composition of the PFOC determines the choice of a particular stabilizing agent.

At present for the preparation of emulsions of rapidly eliminable PFOCs expensive phospholipids of organic origin are used, that have a high affinity for lipophilic PFOCs and require antioxidant additives for preventing peroxide oxidation. In the case of preparing binary compositions from two PFOCs relatively close in lipophilic-lipophobic properties (perfluorodecalin and perfluorotripropylamine), a mixture of phospholipids with a polyoxyethylene-polyoxypropylene copolymer is used [USSR Patent No. 797546, belongs to Green Cross Corp.]. A synthetic cheap polyoxyethylene-polyoxypropylene copolymer is used for stabilizing emulsions containing lipophobic PFOCs. Such stabilizers are, for instance, perfluorobutylamine which is not eliminable from the organism of animals and therefore is used only in experimental pharmacology and physiology, or PFMCP and, less successfully, mixtures of PFD with PFMCP. The PFOC composition proposed in the present invention, consisting of a mixture of several PFOCs with gradually changing lipophilic-lipophobic properties is also adequately stabilized in an emulsified form by a polyoxyethylene-polyoxypropylene copolymer, which makes the emulsion essentially cheaper and allows taking simple measures for minimizing the danger of the origination of hydroperoxides in the course of manufacturing and storing the emulsion, without additionally introducing antioxidants into the formulation.

The second object of the present invention is accomplished by that in the known process for the preparation of a PFOC emulsion, which comprises mixing depyrogenized components by passing liquid PFOCs through an aqueous solution of a stabilizing agent and multiple homogenizing of the resultant mixture in a two-circuit high-pressure homogenizer, according to the invention, before mixing the components, a mixture of liquid PFOCs and an aqueous solution of a stabilizing agent are saturated with carbon dioxide gas, after that the aqueous solution of the stabilizing agent is heated at a temperature not exceeding 75° C., then the mixture of liquid PFOCs is introduced in several jets into the cooled aqueous solution of the stabilizing agent under intensive stirring and feeding carbon dioxide gas, simultaneously passing the resulting coarse-dispersed pro-emulsion several times through the first circuit of the homogenizer, whereafter the finely divided pro-emulsion is subjected to homogenization in the second circuit of the homogenizer till the required dispersity is obtained with feeding carbon dioxide gas, and an aqueous-saline composition is added. The obtained medicinal form is poured into containers.

Saturating the components to be mixed with carbon dioxide gas makes it possible to provide conditions under which in the course of manufacturing the emulsion the formation of peroxide compounds is minimized, the presence of which, as well as the presence of coarse particles, brings about the origination of reactogenicity of emulsions (Table 5). Under experimental conditions the presence of reactogenicity was judged from the drop in the content of neutrophilic leukocytes in the peripheral blood of the rabbit after administering the emulsion in the dose of 10 ml per kg of the body weight. Quantitatively the degree of reactogenicity was calculated from the value of the neuroleptic index: an increase of the neuroleptic index by more than 3 units is indicative of a noticeable reactogenicity of the emulsions [M. V. Berkos, Emulsions of Perfluorocarboh Compounds in Experimental Intravenous Administration. Abstract of Candidate's Thesis, Leningrad, 1991].

Warming-up of the aqueous solution of the stabilizing agent (proxanol) makes it possible to depyrogenize the solution without passing it through sorbents which impair the quality of the stabilizing agent and change its molecular-mass distribution and the surface-active properties. Deviations from the indicated temperature values impair the surface-active properties of the stabilizing agent or increase the content of hydroperoxides in it.

Jet-like introducing of liquid PFOCs into the aqueous solution of the stabilizing agent with intensive stirring and simultaneous passing the resulting mixture through the high-pressure homogenizer contributes to speeding-up the process of preparing the pro-emulsion. The rate of PFOC feeding, stirring and passing the mixture through the homogenizer is regulated in such a manner that the formation of the macroscopic PFOC/water interface is precluded, this being a prerequisite for obtaining a monodisperse emulsion.

Owing to sequential use of two homogenizer circuits, the number of recirculation cycles, compared with the prototype, is reduced from 12 to 9.

Thus, the proposed process makes it possible to obtain large lots of emulsions, to minimize the formation of peroxide compounds, while preserving a high monodispersity of the emulsion particles on the level of 0.05–0.1 μm (Table 6).

The use of a mixture of underrefined perfluorocarbons and perfluorinated tertiary amines instead of individual highly purified PFOCs, as well as a simpler and more rapid technology provides a possibility to accomplish the third object of the invention: to cut down expenses for manufacturing the emulsion and to reduce the cost of the preparation at least 2- or 5-fold, simultaneously enhancing the stability and improving the rheological properties of the emulsions. Thereby prospects are opened for industrial manufacturing and wider uses of PFOC emulsions in clinical practice.

BRIEF DESCRIPTION OF THE DRAWINGS

The invention is further explained by a description of exemplary embodiments thereof and by the accompanying drawings, in which.

Figure 1:
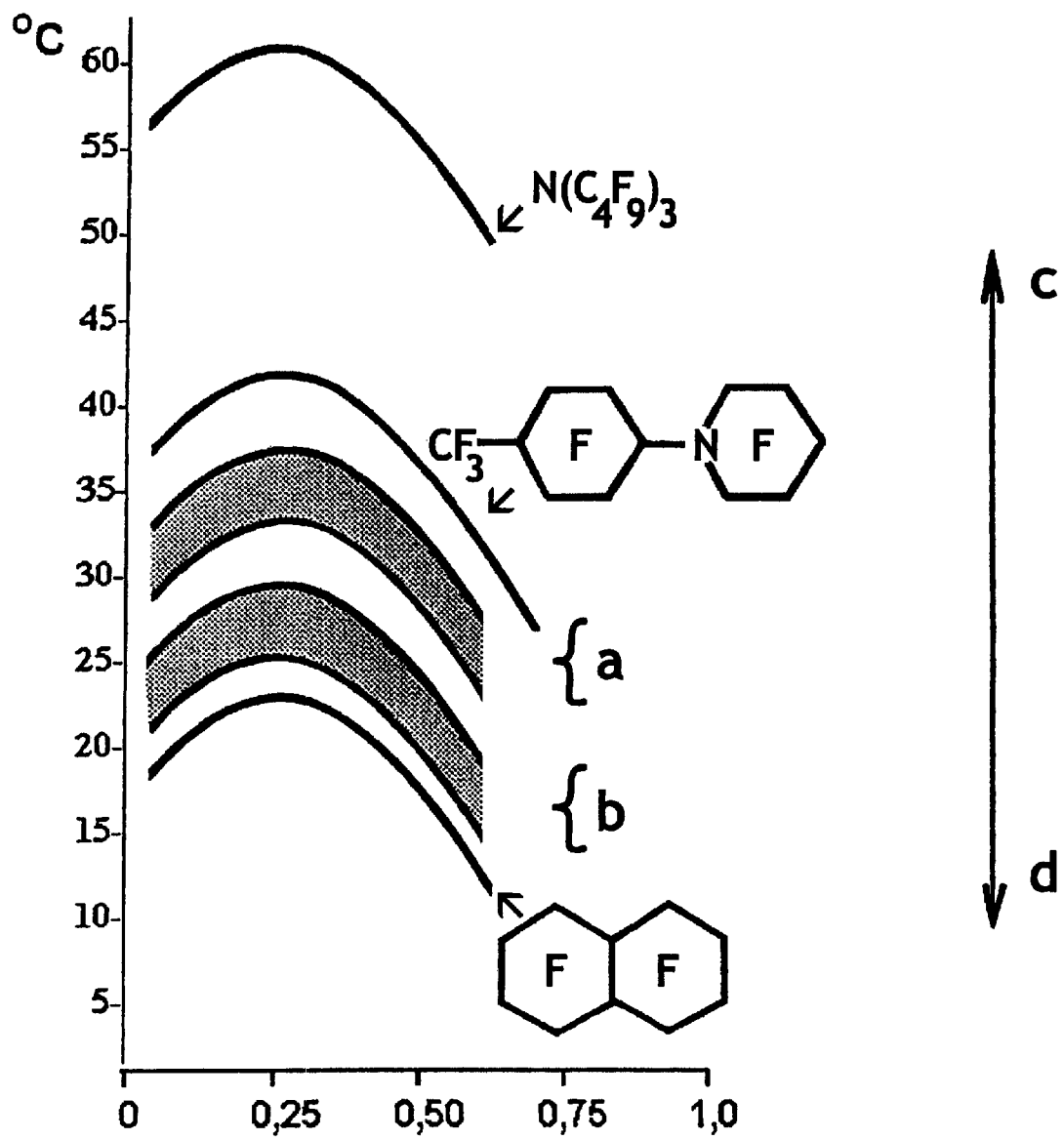
FIG. 1 shows temperature-composition phase diagrams of two-component PFOC-hexane systems, wherein the temperature in ° C. is plotted along the Y-axis and the proportion of PFOCs in the two-component system in relative units is plotted along the X-axis.

The essence of the invention is explained by FIG. 1, in which temperature-composition phase diagrams of two-component PFOC-hexane systems are presented for different kinds of PFOCs, including those entering into the PFOC emulsion formulation being patented.

The zone for PFMCP admixtures is shown at "a", the zone for PFD admixtures is shown at "b", arrow "c" indicates the direction to the area of lipophobic slowly eliminable PFOCs, and arrow "d" indicates the direction to the area of lipophobic rapidly eliminable PFOCs.

It is seen that PFMCP admixtures and PFD admixtures occupy an intermediate position in respect of the phase diagrams and critical temperatures of dissolution in hexane. Consequently, the composition of PFOCs in the emulsion particles is a mixture of substances with gradually changing properties, this ensuring their full-value mutual dissolution, without forming separate clusters which disturb the homogeneity and stability of the emulsion particles.

Figure 2:
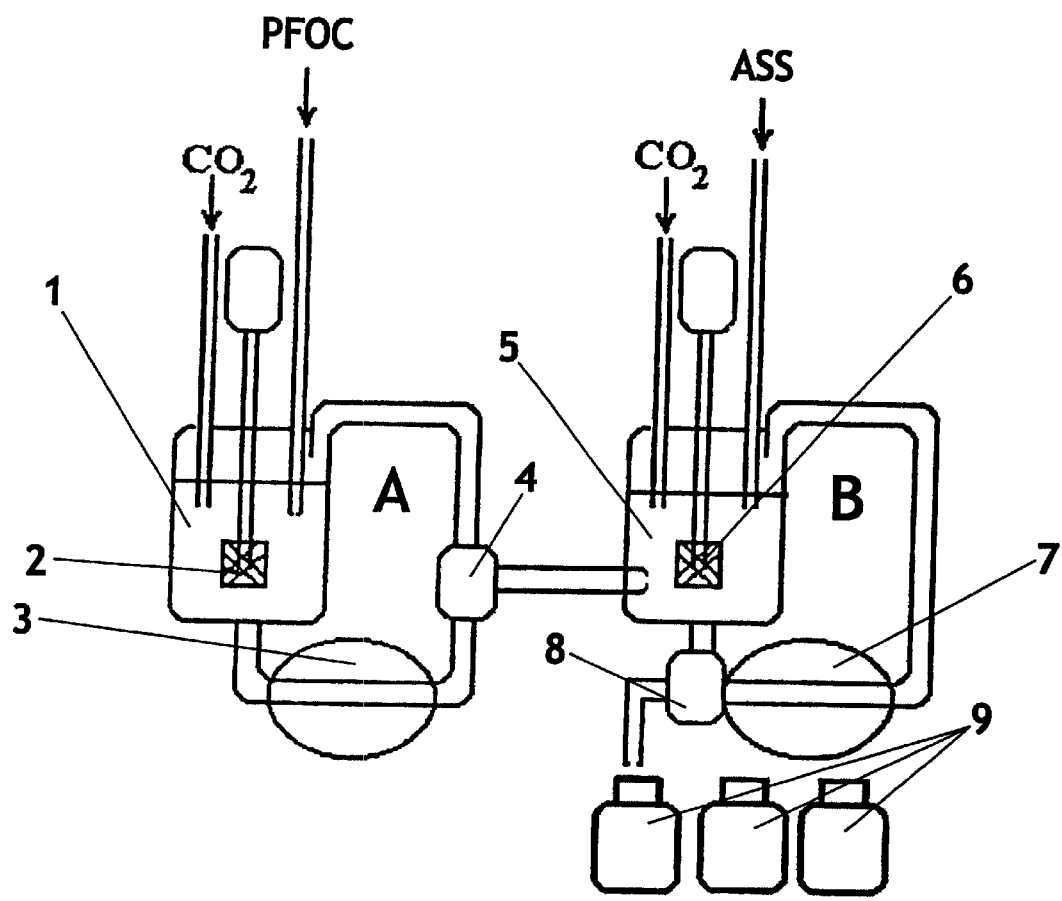
FIG. 2 shows a diagram of a device for preparing a medicinal form of the PFOC emulsion, according to the invention.

The essence of the process being patented is illustrated by FIG. 2, wherein a homogenizer is shown diagrammatically with a first circuit A and a second circuit B. The first circuit A comprises a thermostated reactor 1 with a high-speed stirrer 2, a high-pressure chamber 3, a selector valve 4. The second circuit B comprises a thernostated reactor 5 with a high-speed stirrer 6, a high-pressure chamber 7, and outlet selector valve 8 and receiving containers 9.

The process of preparing the PFOC emulsion is carried out in the following manner. The thermostated reactor 1 of the first circuit of the homogenizer is charged with an aqueous solutionl of a stabilizing agent, saturated withcarbon dioxide gas, and heated for 12–14 hours at a temperature not higher than 75° C. Then the stabilizer agent solution is cooled down, and a mixture of sterilized depyrogenized PFQCs saturated with carbon dioxide gas is fed jetwise, with the high-speed stirrer 2 switched on, into said solution. The resulting coarse pro-emulsion is passed several times through the hirst high-pressure chamber 3 at a pressure of 300–400 kg/cm$^2$ with constant feeding carbon dioxide gas into the reactor. Then the stream of the pro-emulsion is directed with the help of the valve 4 to the second therpmostated reactor 5 of the second circuit of the homogenizer and passed several times. through the second high-pressure chamber 7 at a pressure of 400–500 kg/cm$^2$ till particles of a required size are obtained. The process of homogenization is conducted with constant cooling of the reactors and with feeding carbon dioxide gas into both reactors. Then a sterile apyrogenic aqueous-saline solution (ASS), with the stirrer 6 switched on, is fed into the reactor 5, and after said solutiohis stirred uniformly with the PFOC mixture, the resulting medicinal form of the PFOC emulsion is directed with the help of the valve 8 to dispensing into the receiving containers 9.

It is known to use emulsions of perfluoroorganic compounds for treating anemias of different genesis, hemorrhagic, traumatic, burn, cardiogenic shack ischemic injuries of the heart and brain, craniocerebral injuries, disturbances of the coronary and cerebral blood flow, as a highly effective perfusion medium for the preservation of organs intended for transplantation, for the perfusion and perfusionless anti-ischemic protection of the myocardium in reparative operations on the heart, for use in artificial circulation apparatus, in regional perfusion of extremities when carrying out chemo- and radiotherapy, as contrast media in X-ray, ultrasonic and NMR diagnoses of vascular diseases, as means for acting on the immune system, and also in pharmacological, physiological and biophysical investigations carried out on organs subjected to perfusion.

It is proposed to use the emulsion obtained by us, in addition to the above-cited applications, for treating air-and-fat vascular embolism, obliterating vascular diseases of extremities, for the detoxication in the case of poisoning with lipophilic toxic compounds, and for the prophylaxis of toxic injuries caused by various xenobiotics.

DETAILED DESCRIPTION OF THE INVENTION

The invention is explained by the Examples which are given hereinbelow and are intended to demonstrate the possibility of carrying out the invention only in particular embodiments thereof.

EXAMPLE 1

Preparing a preferred variant of the PFOC emulsion composition.

The thermostated reactor 1 was charged with 1.8 l of a 10% sterile aqueous solution of a stabilizing agent with the molecular mass of 8000 Da, saturated with carbon dioxide gas, heated for 12 hours at the temperature of 70° C., and after cooling the stabilizing agent solution, the high-speed stirrer 2 was switched on, and 200 ml of a mixture of sterile apyrogenic PFOC saturated with carbon dioxide gas, were fed in two jets into the reactor. The mixture comprised rapidly eliminable perfluorocarbons and slowly eliminable perfluorinated tertiary amines taken in the 2:1 ratio, namely, perfluorodecalin in an amount of 6.0 vol. % with admixtures of perfluoromethylindane, perfluoro-1-methyl-3-propylcyclohexane, trans-perfluoroindane, perfluoro-4-oxodecalin, perfluorobutylcyclohexane, perfluoropropylcyclohexane, perfluoroethylcyclohexane, perfluorobutylcyclopentane, cis-perfluoro-1-methyl-2-etylcyclohexane in the total amount of 0.7 vol. %, perfluoro-N-4-(methylcyclohexyl)-piperidine in an amount of 2.3 vol. % with admixtures of perfluoro-N-(4-methylcyclohexyl)-2-methylpyrrolidine, perfluoro-methylbutyl-cyclohexyl)-amine, cis- and trans-isomers of perfluoromethylpropyl-(4-methylcyclohexyl)-amine, isomers of perfluoromethylpropyl-(methyl-cyclopentyl)-amine and perfluoro-N-(4-methylcyclohexyl)-1-methylpiperidine, in the total amount of 1.0 vol. %, and also 0.02 vol. % of H-perfluoroalkanes. The forming coarse pro-emulsion were passed four times through a high-pressure chamber 3 of the first circuit of the homogenizer at the pressure of 350 kg/cm$^2$ and then five times through the high-pressure chamber 7 of the second circuit of the homogenizer at the pressure of 450 kg/cm$^2$ and temperature of 18–22° C. and with a constant feed of carbon dioxide gas. In the reactor 5 of the second circuit of the homogenizer the obtained submicron emulsion was mixed with a concentrated aqueous-saline formulation, so that the finished medicinal form of the emulsion contained 10 vol. % of PFOC, 4% of the stabilizing agent, 102 mM of NaCl, 5.2 mM of KCl, 1.8 mM of MgCl$_2$, 7.7 mM of NaHCO$_3$, 1.65 mM of NaH$_2$PO$_4$ and 11 mM of D-glucose. The finished packaged preparation is a composition isosmotic with blood plasma with the osmotic pressure of 280 mOcm, viscosity of 2.5 cP, pH 7.3, at the concentration of free fluorine ions of $5.10^{-6}$ M and of peroxide compounds of 50 μm. The mean size of the emulsion particles was 0.07 μm, the admixture of 0.2–0.3 μm particles was less than 1% in computer electron-microscopic control. The LD$_{50}$ value for mice in intraperitoneal administration was 160 ml/kg. The survival of rabbits after 5-fold intravenous administration of 20 ml with a 1 week interval was 100% after 3 months of observations. After storing the emulsion in frozen form and fivefold freezing-defrosting thereof the size of the emulsion particles was 0.11 μm (Table 4).

EXAMPLE 2

The emulsion was prepared as described in Example 1, but with the ratio of the rapidly and slowly eliminable PFOCs 3:1, with the amount in the composition of rapidly eliminable perfluorocarbons 6.4% of perfluorodecalin and 1.1% of admixtures of perfluoromethylindane, perfluoro-1-methyl-3-propylcyclohexane, trans-perfluoroindane, perfluoro-4-oxodecalin, and in the composition of slowly eliminable PFOCs 1.8% of perfluoro-N-(4-methylcyclohexyl)-piperidine and 0.7% of admixtures of perfluoro-N-(4-methylcyclohexyl)-2-methylpyrrolidine, perfluoromethylbutyl-(4-methyl-cyclohexyl)-amine, cis- and trans-isomers of perfluoromethyl-propyl-(4-methylcyclohexyl)-amine, and also 0.01 vol. % of H-perfluoroalkanes. The pro-emulsion was passed three times through the high-pressure chamber 3 of the first circuit of the homogenizer at the pressure of 450 kg/cm$^2$, the emulsion was passed five times through the high-pressure chamber 7 of the second circuit of the homogenizer at the pressure of 550 kg/cm$^2$. The mean diameter of the particles of the obtained PFOC emulsion was 0.07 μm, the proportion of 0.2–0.3 μm-diameter particles was 0.9%. The LD$_{50}$ value for mice was 150 mg per kg of the body weight. An apyrogenic PFOC emulsion was obtained with the concentration of peroxide compounds of 75 mM. The survival of rabbits after intravenous administration of 20 ml of the PFOC emulsion per kg was 100% during 90 days of observations.

The emulsion was used for the replacement of 55% blood losses in dogs and for 65% blood substitution in rats. The survival of the animals was 100%.

EXAMPLE 3

The PFOC emulsion was prepared as described in Example 2 and used as a perfusion composition for the preservation of a canine kidney in a recirculatory regime in normothermal perfusion. The time of preservation of the kidney before the perfusion pressure buildup (before the development of a tissue edema) was 36 hours. In the course of perfusion the emulsion was changed every 9 hours. In grafting the kidney to be perfused to a recipient dog, the transplant started excreting urine immediately after the restoration of the blood flow.

EXAMPLE 4

The emulsion was prepared as described in Example 1, but a polyoxyethylene-polyoxypropylene copolymer with the average molecular mass of 6 thousand Da was used as the stabilizing agent, the PFOC pro-emulsion was finely divided in the chamber 3 of the first circuit of the homogenizer at the pressure of 500 kg/cm$^2$, the emulsion was finely divided in the chamber 7 of the second circuit of the homogenizer at the pressure of 550 kg/cm$^2$, the aqueous-saline formulation of the finished medicinal form of the PFOC emulsion comprised 102 mM of NaCl, 5.2 mM of KCl, 1.8 mM of $MgCl_2$, 7.7 mM of $NaHCO_3$, 1.65 mM of $NaH_2PO_4$, and 11 mM of D-glucose, 5 mM of sodium pyruvate, 5 mM of sodium β-oxybutyrate, 5 mM; of sodium succinate, 5 mM of sodium glutamate, 5 mM of taurine. The mean diameter of the particles of the obtained PFOC emulsion was 0.06 μm, the proportion of the 0.2–0.3 μm-diameter particles was 1.1%. The $LD_{50}$ for mice was 130 ml per kg of the body weight. The concentration of peroxide compounds was 100 μM. The. emulsion was used for pharmaco-ice-chip cardioplegia. A canine heart was isolated in a single heart-lung apparatus and perfused with the PFOC emulsion cooled down to 16° C. for 30 minutes. Then the heart was disconnected from the perfusion system and kept immersed into the PFOC emulsion at the temperature of 6° C. for 4 hours. After that the heart was coupled to the perfusion system filled with the PFOC emulsion and perfused for 15 at 16° C., whereafter the heart was coupled to the femoral vessels of a recipient dog. On four out of six cases the electric and contractile activity of the heart restored upon transplantation without additional electrostimulation; in two cases after the first discharge of an electrostimulater. In all the cases no symptoms of cardiac insufficiency were observed.

EXAMPLE 5

A method of treating air-and-fat vascular embolism. Air-and-fat embolism was induced in the experiment by administering intravenously to rabbits 10 ml of a coarse-dispersed emulsion of corn oil in water with 10 to 300 μm particles and with fine air bubbles. The experiment was carried out on 22 animals weighing 3–3.5 kg. The PFOC emulsion prepared in accordance with the procedure described in Example 2, was administered to the rabbit intravenously 20 minutes after the loss of consciousness or 3–4 minutes after the disturbance of the respiration rhythm or respiratory standstill. The treatment of fat and air embolism is based on using to advantage an extremely large sorption surface of the emulsion particles, a relative excess of the surfactant in the adsorption layer of the particles and in the aqueous phase, the ability of highly dispersed particles to penetrate into partly obturated vessels and to induce emulsification, reduction of the size and sorption of fat and air drops, as a result of which the patency of the vessels and the mass metabolism are restored. The curative effectiveness of the PFOC emulsion manifested itself in bringing animals out of coma and the state of clinical death resulting from the respiratory standstill because of the blood flow disturbance in the brain of animals. Before administering the whole amount of the PFOC emulsion (10–15 ml per kg of the body weight) was completed, rabbits regained consciousness, opened their eyes, papillary reflexes became restored. Administering the PFOC emulsion after the disturbance of respiration contributed to the restoration of even breathing of the animals during several minutes and ensured restoration of independent breathing in the case of respiration standstill and coupling the animal to an apparatus for artificial ventilation of the lungs.

EXAMPLE 6

A method of treating obliterating vascular injury of extremities. Obliterating atherosclerosis was rmodeled in rabbits by overfeeding them with substances enriched with products with a high content of cholesterol. The Theological characteristics of the blood flow in extremities were determined by ultrasound Doppler echography, and the dynamics of partial oxygen pressure ($pO_2$) in the tissues of the femur and crus of the hind leg was determined with the help of noninvasive sensors. For comparing the curative effect, intravenous administration of rheopolyglucinum, a well-known rheologically active preparation, was used. The rheopolyglucinum (5 ml per kg of the body weight) improved the blood flow by 10±3% and increased the tissue $pO_2$ on an average by 6±2%. After the intravenous administration of the PFOC emulsion in the dose of 5 ml per kg of the body weight, an improvement of the blood flow was also observed, like after the administration of rheopolyglucinum, but in this case the value of the tissue $pO_2$ pressure increased by 25±5% (p<0.02).

EXAMPLE 7

A method of treating toxic injuries caiused by lipophilic compounds. The PFOC emulsion prepared as described in Example 1 was used as a means sorbing lipophilic compounds which have entered the blood flow, for instance, ethanol. Thereby the acting concentration of these lipophilic compounds is reduced and their entrance into the tissues is slowed down. A lethal dose of 33% aqueous ethanol was administered per os to ten rats with a body weight of 250–290 g in dosage of 4 g of ethanol per kg of body weight. 8 animals died. Ten rats of the second group, after administration of a lethal dose of ethanol to them, were administered intravenously the PFOC emulsion in dosage of 5 ml per kg of body weight. Only 1 rat died.

EXAMPLE 8

A method of preventing toxic injuries

A). The PFOC emulsion prepared as described in Example 1 was used as a means which inhibits in early periods after the accumulation of PFOCs in the liver the functioning of the monooxygenase system of the liver, for decreasing the injurious effect of heterblogous xenobiotics whose metabolic products have a greater toxicity than the starting substances. In an experiment on rats, for decreasing toxic consequences of ether anesthesia, inhibition of the detoxication function of the liver was induced by intravenous administration of the PFOC emulsion 6 hours before the ether anesthesia. Inhibition of the ethyl ether metabolism decreases the rate of formation of ether hydroxylation products which are more toxic than the ether itself. In rats not pretreated with the PFOC emulsion a twofold overdosage with ether anesthesia during one day caused the development of, pronounced fat infiltration and diffuse dystrophic changes in the liver tissue during 3–4 days. If the animals were administered intravenously the PFOC emulsion in a dose of 5–7 ml per kg of body weight 6 hours before the first ether anesthesia, then the subsequent twofold overdosage of the ether anesthesia caused only insignificant diffuse changes of the liver without development of the fat infiltration of the tissue.

B). The PFOC emulsion prepared as described in Example 1 was used as a means activating in the late periods after the PFOC accumulation in the liver the functioning of the monooxygenase system of the liver for decreasing the injurious effect of heterologous xenobiotics whose metabolic products have a smaller toxicity than the starting substances. In an experiment on rats, for decreasing toxic consequences of chloroform anesthesia, it was necessary to accelerate the chloroform metabolism in the liver tissue. For this purpose, 4 days before the chloroform anesthesia carried out with an overdosage of up to respiration disturbance, 5 rats were administered intravenously 7 ml of the PFOC emulsion prepared as described in Example 1. One day before the chloroform anesthesia the condition of the liver was checked against the duration of hexenal sleep: this duration decreased to 1.5–3 minutes, i.e., 5- to 7-fold compared with the duration of hexenal sleep in intact animals, which lasted 18–20 minutes, this being, as it was shown earlier by V. V. Obraztsov et al. [Obraztsov V., Sklifas A., Maevskii E., Shekhtrrzn D., Kukushkin N. Is the induction of cytochrome P-450 a cause of rabbit death after injection of perfluorodecalin emulsion? // Cytochrome P-450: Biochemistry and Biophysics. 1992, INCO-TNC, Moscow, 597–600], a consequence of a 2- to 3-fold increase in the amount of cytochrome P-450 of the phenobarbital type in hepatocytes. The liver of the animals not treated with the PFOC emulsion, after the overdosage of the chloroform anesthesia, bore the signs of destruction, swelling of cells and mitochondria, pronounced fat infiltration. In the animals administered with the PFOC emulsion 4 days before the chloroform anesthesia overdosage, in spite of a large dose of chloroform, considerable destruction and fat infiltration of hepatocytes were not observed. The duration of retention of an increased detoxicating activity of the liver approximately coincided with period of half-elimination of the rapidly eliminable PFOCs accumulated by the liver cells after the intravenous administration of the PFOC emulsion.

TABLE 1

Comparison of the toxicity* of PFD and PFMCP differing in the content of admixtures and of emulsions produced from these PFOCs

| Investigated preparation (IP) | Culturing medium/IP ratio | Concentration of fluorine ions ($10^{-6}$ M) | Percentage of increase in the number of cells after cultivation |
|---|---|---|---|
| Culturing medium | — | 1.0 | 100% |
| Mixture of highly purified PFD and PFMCP (according to RF Pat. No. 2070033) | 20:1 | 1.0 | 90 ± 10% |
| Mixture of PFD with admixtures of perfluorocarbons and of PFMCP with admixtures of perfluorinated tertiary amines (according to the invention being patented) | 20:1 | 1.0 | 90 ± 12% |
| PFOC emulsion according to Pat. 2070033 | 10:1 | 4.0 | 70 ± 95% |

TABLE 1-continued

Comparison of the toxicity* of PFD and PFMCP differing in the content of admixtures and of emulsions produced from these PFOCs

| Investigated preparation (IP) | Culturing medium/IP ratio | Concentration of fluorine ions ($10^{-6}$ M) | Percentage of increase in the number of cells after cultivation |
|---|---|---|---|
| PFOC emulsion according to the invention being patented | 10:1 | 5.0 | 70 ± 95% |

*The toxicity of PFOC was estimated from the suppression of growth of cultivated transformed lymphoid cells of Raji line

TABLE 2

Comparison of the toxicity of different PFOC emulsions from the value of the half-lethal dose for mice and from the survival of rabbits

| Investigated preparation | Acute toxicity for mice $LD_{50}$ in ml per kg | Survival of rabbits (in %), 180 days after intravenous administration of investigated preparations (single dose-20 ml per kg of body weight) | |
|---|---|---|---|
| | | Single administration | 20-fold administration |
| Control: aqueous-saline composition agent | >200 | 100.0 | 100.0 |
| PFD emulsion | 150 | 0.0 | * |
| PFD/PFMCP emulsion (3:1 ratio) | 140 | 10.0 | * |
| PFD/PFMCP emulsion (2:1 ratio) according to RF Pat. No. 2070033 | 140 | 10.0 | 60.0 |
| PFOC emulsion according to the invention being patented | 140 | 100.0 | 100.0 |

Repeated administration cannot be performed, because animals die after single administration of the preparation.

TABLE 3

Solubility of some PFOCs in olive oil lipids and in membranes of erythrocytes at 37° C.

| Type of PFOC | Solubility in oil (mM) | Solubility in membranes (ml per kg of dry membranes) |
|---|---|---|
| Perfluorodecalin (PFD) | 26.0 | 2.0 |
| PFD admixtures | 17.0?22.0 | 1.4 |
| Perfluoromethyl-N-(4-cyclohexyl)-piperidine PFMCP | 7.6 | 0.5 |
| PFMCP admixtures* | 9.5?12.0 | 0.8 |
| Perfluorotripropylamine | 5.1 | 0.3 |
| Perfluorotributylamine | 1.2 | 0.08 |

*PFD admixtures and PFMCP admixtures are cited in the text of the description of the preferred embodiment of the invention.

TABLE 4

Comparison of the stability of the emulsion according to RF Patent No. 2070033 and of the claimed emulsion

| Kind of PFOCs in the composition of emulsions | Average size of emulsion particles, μm, (according to electron microscopy data with contrasting with uranyl acetate) | | | Optical density (D per 540 μm) after mixing with different concentrations of dextran in 1:1 ratio | | | Viscosity, in cP |
|---|---|---|---|---|---|---|---|
| | Initial | After 45 days of storage at 4° C. | After 5-fold freezing and defrosting | Without dextran | 3% dextran | 6% dextran | |
| Mixture of highly purified PFD and PFMCP in 2:1 ratio | 0.08 ± 0.01 | 0.16 ± 0.02 | 0.14 ± 0.02 | 0.09 | 0.37 | 0.90 | 2.7 |
| Mixture of PFD with admixtures* and PFMCP with admixtures in 2:1 ratio | 0.08 ± 0.01 | 0.12 ± 0.01 | 0.11 ± 0.01 | 0.09 | 0.18 | 0.64 | 2.5 |

*PFD admixtures and PFMCP admixtures are cited in the text of the description of the preferred embodiment of the invention.

TABLE 5

The value of neutropenic index as an indicator of reactogenicity of compared PFOC emulsion samples

| Investigated preparation | Neutropenic index (after M.V. Berkos) | |
|---|---|---|
| | Freshly prepared preparation | After 6 months of storage in frozen form |
| PFOC emulsion according to PF Pat. No. 2070033 | 2.5 ± 0.3 | 4.2 ± 0.5 |
| PFOC emulsion according to the invention being patented | 1.8 ± 0.2 | 3.0 ± 0.4 |
| Control (aqueous-saline composition with 4% of stabilizing agent) | 1.3 ± 0.1 | 1.4 ± 0.2 |

TABLE 6

Comparison of the main parameters of the PFOC emulsion according to RF Pat. No. 2070033 and of the emulsion according to the invention being patented

| Compared parameter | Values of parameters and characteristics | |
|---|---|---|
| Form of PFOC emulsion | According to RF Pat. No. 2070033 | According to the invention being patented |
| Form of PFOCs | Mixture of individual highly purified PFD and PFMCP | Mixture of PFD and PFMCP with admixtures of rapidly and slowly eliminable PFOCs |
| Cost of PFOCs | Cost of the prototype is assumed to be 100% | <40% of the cost of the prototype |
| Operation and time of preparing 20 l of pro-emulsion | Dropwise adding of PFOCs to surfactant solution-180–200 min. | Multijet introducing of PFOCs into surfactant solution-15–20 min. |
| Concentration of peroxide radicals in emulsion | $2.6 \cdot 10^4$ M | $2.1 \cdot 10^{-5}$ M |
| Number of recirculation cycles in homogenization | 12 | Not over 9 |
| Total time of preparing 40 l of PFOC emulsion | 8 hours | 3.5 hours |
| Relative viscosity (η), cP | 3.5 | 2.5 |
| Average size of particles, μm | 0.08 p 0.1 | 0.05 p 0.1 |
| Absolute oxygen capacity ($VO_2$) at t 25° C. and $pO_2$ 760 mm Hg | 6.9 vol. % | 6.9 vol. % |
| Dynamic oxygen capacity ($VO_2/\eta$) | 1.97 | 2.76 |
| Time of semi-elimination from blood flow in rats, h | 6.0 ± 0.5 | 9.5 ± 1.0 |

Industrial Applicability

An emulsion of perfluoroorganic compounds, according to the invention, is intended for intravascular administration in replacing blood losses, for treating various disases accompanied by hypoxic or ischemic injuries, and also for use as contrast and perfusion media.

What is claimed is:

1. An emulsion of perfluoroorganic compounds (PFOC) comprising a rapidly eliminable perfluorocarbon (PFC) and a perfluorinated cyclic tertiary amine (PFCTA), a stabilizing agent, a physiologically acceptable aqueous-saline solution with a substrate of energy metabolism, further comprising admixtures of at least three rapidly eliminable perfluorocarbons (PFC) $C_7$–$C_{10}$ with the critical temperature of dissolution in hexane (CTDH) higher than the CTDH of the main PFC by not more than 8° C., and at least three slowly eliminable perfluorinated cyclic tertiary amines (PFCTA) $C_{11}$–$C_{13}$ with the CTDH lower than the CTDH of the main PFCTA by not more than 10° C., and minor admixtures of H-perfluoroalkanes, wherein the content of admixtures of the rapidly eliminable perflurocarbons (PFC) does not exceed 15% of the content of the main perfluorocarbon (PFC), and wherein the content of admixtures of the slowly eliminable perfluorinated cyclic tertiary amines (PFCTA) does not exceed 50% of the content of the main perfluorinated cyclic tertiary amine (PFCTA), and wherein the content of admixtures of H-perfluoroalkanes does not exceed 0.1 vol. %.

2. The PFOC emulsion of claim 1 comprising:
- a main rapidly eliminable perfluorocarbon in the form of a mixture of cis- and trans-isomers of perfluorodecalin in an amount of 6 vol. %;
- admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
- a main slowly eliminable perfluorinated tertiary amine in the form of a mixture of isomers of perfluoro-N-4-(methyl-cyclohexyl)piperidine in an amount of 2.3 vol. %;
- admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl) amine and perfluoro-N-(4-methylcyclohexyl)-1-methylpiperidine in a total amount of 1.0 vol. %;
- wherein the content of H-perfluoroalkanes is 0.02 vol. %; and
- the ratio of polyoxyethylene and polyoxypropylene blocks in the copolymer is 4:1 with the molecular mass of 8,000 Da.

3. The emulsion of claim 1, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, and 11 mM of D-glucose.

4. The emulsion of claim 1, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

5. The PFOC emulsion of claim 1, wherein the physiologically acceptable aqueous-saline solution comprises NaCl, KCl, $MgCl_2$, $NaHCO_3$, $NaH_2PO_4$ and D-glucose.

6. The PFOC emulsion of claim 5, comprising:
- a main rapidly eliminable perfluorocarbon in the form of a mixture of cis- and trans-isomers of perfluorodecalin in an amount of 6 vol. %;
- admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
- a main slowly eliminable perfluorinated tertiary amine in the form of a mixture of isomers of perfluoro-N-4-(methyl-cyclohexyl)piperidine in an amount of 2.3 vol. %;
- admixtures of perfluorinated tertiary amines, comprising a mixture of perfluoro-N(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)-amine and perfluoro-N-(4-methylcyclohexyl)-1-methylpiperidine in a total amount of 1.0 vol. %;
- wherein
  - the content of H-perfluoroalkanes is 0.02 vol. %; and
  - the ratio of polyoxyethylene and polyoxypropylene blocks in the copolymer is 4:1 with the molecular mass of 8,000 Da.

7. The PFOC emulsion of claim 1, wherein the main rapidly eliminable PFC is a mixture of isomers of perfluorodecalin in the form of cis- and trans-forms with the the CTDH of 22–23° C.

8. The PFOC emulsion of claim 7, wherein the ratio of the rapidly eliminable and slowly eliminable PFOCs is 2:1 or 3:1.

9. The PFOC emulsion of claim 7, wherein a polyoxyethylene-polyoxypropylene copolymer with a molecular mass of 6,000–10,000 Da is used as the stabilizing agent.

10. The PFOC emulsion of claim 7, wherein the physiologically acceptable aqueous-saline solution comprises NaCl, KCl, $MgCl_2$, $NaHCO_3$, $NaH_2PO_4$ and D-glucose.

11. The PFOC emulsion of claim 7, comprising:
- a main rapidly eliminable perfluorocarbon in the form of a mixture of cis- and trans-isomers of perfluorodecalin in an amount of 6 vol. %;
- admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cisperfluoro-1-methyl-2-ethylcyclohexane in an amount of 0.7 vol. %;
- a main slowly eliminable perfluorinated tertiary amine in the form of a mixture of isomers of perfluoro-N-4-(methylcyclohexyl)piperidine in an amount of 2.3 vol. %;
- admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)amine and perfluoro-N-(4-methylcyclohexyl)-1-methylpiperidine in a total amount of 1.0 vol. %;
- wherein
  - the content of H-perfluoroalkanes is 0.02 vol. %;
  - the ratio of polyoxyethylene and polyoxypropylene blocks in the copolymer is 4:1 with the molecular mass of 8,000 Da.

12. The emulsion of claim 8, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$ and 11 mM of D-glucose.

13. The emulsion of claim 7, wherein the aqueous-saline solution comprises 102 mM of NaCl, 5.2 mM of KCl, 1.8 mM of MgCl2, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

14. The PFOC emulsion of claim 1, wherein the main slowly eliminable PFCTA is a mixture of isomers of perfluoro-N-4-(methylcyclohexyl)-piperldine with CTDH of 41–42° C.

15. The PFOC emulsion of claim 14, wherein the ratio of the rapidly eliminable and slowly eliminable PFOCs is 2:1 or 3:1.

16. The PFOC emulsion of claim 14, wherein a polyoxyethylene-polyoxypropylene copolymer with a molecular mass of 6,000–10,000 Da is used as the stabilizing agent.

17. The PFOC emulsion of claim 14, wherein the physiologically acceptable aqueous-saline solution comprises NaCl, KCl, $MgCl_2$, $NaHCO_3$, $NaH_2PO_4$ and D-glucose.

18. The PFOC emulsion of claim 14, comprising:
   a main rapidly eliminable perfluorocarbon in the form of a mixture of cis- and trans-isomers of perfluorodecalin in an amount of 6 vol. %;
   admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cisperfluoro-1-methyl-2-ethylcyclohexane in an amount of 0.7 vol. %;
   a main slowly eliminable perfluorinated tertiary amine in the form of a mixture of isomers of perfluoro-N-4-(methyl-cyclohexyl)piperidine in an amount of 2.3 vol. %;
   admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)-amine and perfluoro-N-(4-methylcyclohexyl)-1-methylpiperidine in a total amount of 1.0 vol. %;
   wherein
      the content of H-perfluoroalkanes is 0.02 vol. %; and
      the ratio of polyoxyethylene and polyoxypropylene blocks in the copolymer is 4:1 with the molecular mass of 8,000 Da.

19. The emulsion of claim 14, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$ and 11 mM of D-glucose.

20. The PFOC emulsion of claim 14, wherein the aqueous-saline solution comprises 102 mM of NaCl, 5.2 M of KCl, 1.8 mM of $MgCl_2$, 7.7 mM of $NaHCO_3$, 1.65 mM of $NaH_2PO_4$ 11 mM of D-glucose, 5 mM of sodium pyruvate, 5 mM of sodium β-oxybutyrate, 5 mM of sodium succinate, 5 mM of sodium glutamate and 5 mM of taurine.

21. The PFOC emulsion of claim 1, wherein the admixtures of rapidly eliminable perfluorocarbons (PFC) $C_7$–$C_{10}$ comprise a mixture of perfluoromethylindane, perfluoro-1-methyl-3-propylcyclohexane, perfluoroindane, perfluoro-4-oxodecalin, perfluorobutylcyclohexane, perfluoropropylcyclohexane, perfluoroethylcyclohexane, perfluorobutylcyclopentane, perfluoro-1-methyl-2-ethylcyclohexane with the CTDH range of 25 to 28° C.

22. The PFOC emulsion of claim 21, wherein the ratio of the rapidly eliminable and slowly eliminable PFOCs is 2:1 or 3:1.

23. The PFOC emulsion of claim 21, wherein a polyoxyethylene-polyoxypropylene copolymer with a molecular mass of 6,000–10,000 Da is used as the stabilizing agent.

24. The PFOC emulsion of claim 21, wherein the physiologically acceptable aqueous-saline solution comprises NaCl, KCl, $MgCl_2$, $NaHCO_3$, $NaH_2PO_4$ and D-glucose.

25. The PFOC emulsion of claim 21, comprising:
   a main rapidly eliminable perfluorocarbon in the form of a mixture of cis- and trans-isomers of perfluorodecalin in an amount of 6 vol. %;
   admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
   a main slowly eliminable perfluorinated tertiary amine in the form of a mixture of isomers of perfluoro-N-4-(methyl-cyclohexyl)piperidine in an amount of 2.3 vol. %;
   admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)-amine and perfluoro-N-(4-methylcyclohexyl)-1-methylpiperidine in a total amount of 1.0 vol. %;
   wherein
      the content of H-perfluoroalkanes is 0.02 vol. %; and
      the ratio of polyoxyethylene and polyoxypropylene blocks in the copolymer is 4:1 with the molecular mass of 8,000 Da.

26. The emulsion of claim 21, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$ and 11 mM of D-glucose.

27. The emulsion of claim 21, wherein the aqueous-saline solution comprises 102 mM of NaCl, 5.2 mM of KCl, 1.8 mM of $MgCl_2$, 7.7 mM of $NaHCO_3$, 1.65 MM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

28. The PFOC emulsion of claim 1, wherein the admixtures of slowly eliminable perfluorinated cyclic tertiary amines (PFCTA) $C_{11}$–$C_{13}$ comprise a mixture of isomers of cis- and trans-forms of perfluoro-N-(4-methylcyclohexyl)-2-methylpyrrolidine, 2 perfluoromethylbutyl-(4-methylcyclohexyl)-amine, perfluoromethylpropyl-(4-methylcyclohexyl)-amine, perfluoromethylpropyl-(methylcyclopentyl)-amine and perfluoro-N-(4-methylcyclohexyl)-1-methylpiperidine with the CTDH range of 32 to 35° C.

29. The PFOC emulsion of claim 28, wherein the ratio of the rapidly eliminable and slowly eliminable PFOCs is 2:1 or 3:1.

30. The PFOC emulsion of claim 28, wherein a polyoxyethylene-polyoxypropylene copolymer with a molecular mass of 6,000–10,000 Da is used as the stabilizing agent.

31. The PFOC emulsion of claim 28, wherein the physiologically acceptable aqueous-saline solution comprises NaCl, KCl, $MgCl_2$, $NaHCO_3$, $NaH_2PO_4$ and D-glucose.

32. The PFOC emulsion of claim 28, comprising:
a main rapidly eliminable perfluorocarbon in the form of a mixture of cis- and trans-isomers of perfluorodecalin in an amount of 6 vol. %;
admixtures of rapidly eliminable perfluorocarbons comprising a mixture of perfluoromethylindane, perfluoro-1-methyl-3-propylcyclohexane, trans-perfluoroindane, perfluoro-4-oxodecalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
a main slowly eliminable perfluorinated tertiary amine in the form of a mixture of isomers of perfluoro-N-4-(methyl-cyclohexyl)piperidine in an amount of 2.3 vol. %;
admixtures of perfluorinated tertiary amines, comprising a mixture of perfluoro-N-(4-methylcyc lohexyl)-2-methylpyrrolidine, perfuoroethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)amine and perfluoro-N-(4-methylcyclohexyl)-1-methylpiperidine in a total amount of 1.0 vol. %;
wherein
the content of H-perfluoroalkanes is 0.02 vol. %; and
the ratio of polyoxyethylene and polyoxypropylene blocks in the copolymer is 4:1 with the molecular mass of 8,000 Da.

33. The emulsion of claim 28, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$ and 11 mM of D glucose.

34. The emulsion of claim 28, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

35. The PFOC emulsion of claim 1, wherein the ratio of the rapidly eliminable and slowly eliminable PFOCs is 2:1 or 3:1.

36. The PFOC emulsion of claim 35, wherein the physiologically acceptable aqueous-saline solution comprises NaCl, KCl, $MgCl_2$, $NaHCO_3$, $NaH_2PO_4$ and D-glucose.

37. The PFOC emulsion of claim 35, comprising:
a main rapidly eliminable perfluorocarbon in the form of a mixture of cis- and trans-isomers of perfluorodecalin in an amount of 6 vol. %;
admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
a main slowly eliminable perfluorinated tertiary amine in the form of a mixture of isomers of perfluoro-N-4-(methyl-cyclohexyl)piperidine in an amount of 2.3 vol. %;
admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)amine and perfluoro-N-(4-methylcyclohexyl)-1-methylpiperidine in a total amount of 1.0 vol. %;
wherein
the content of H-perfluoroalkanes is 0.02 vol. %; and
the ratio of polyoxyethylene and polyoxypropylene blocks in the copolymer is 4:1 with the molecular mass of 8,000 Da.

38. The emulsion of claim 35, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, and 11 mM of D-glucose.

39. The emulsion of claim 35, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

40. The PFOC emulsion of claim 1, wherein a polyoxyethylene-polyoxypropylene copolymer with a molecular mass of 6,000–10,000 Da is used as the stabilizing agent.

41. The PFOC emulsion of claim 40, wherein the content of the stabilizing agent is 2–4%.

42. The PFOC emulsion of claim 40, wherein the physiologically acceptable aqueous-saline solution comprises NaCl, KCl, $MgCl_2$, $NaHCO_3$, $NaH_2PO_4$ and D-glucose.

43. The PFOC emulsion of claim 40, comprising:
a main rapidly eliminable perfluorocarbon in the form of a mixture of cis- and trans-isomers of perfluorodecalin in an amount of 6 vol. %;
admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cis-perfluoro-1-methyl-2-ethylcyclohexane in an amount of 0.7 vol. %;
a main slowly eliminable perfluorinated tertiary amine in the form of a mixture of isomers of perfluoro-N-4-(methyl-cyclohexyl)piperidine in an amount of 2.3 vol. %;
admixtures of perfluorinated tertiary amines, comprising a 10 mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)amine and perfluoro-N-(4-methylcyclohexyl)-1-methylpiperidine in a total amount of 1.0 vol. %;
wherein
the content of H-perfluoroalkanes is 0.02 vol. %; and
the ratio of polyoxyethylene and polyoxypropylene blocks in the copolymer is 4:1 with the molecular mass of 8,000 Da.

44. The emulsion of claim 40, wherein the aqueous saline solution comprises 102 mM of NaCl, 5.2 mM of KCl, 1.8 mM of $MgCl_2$, 7.7 mM of $NaHCO_3$, 1.65 mM of $NaH_2PO_4$, and 11 mM of D-glucose.

45. The emulsion of claim 40, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

46. The PFOC emulsion of claim 1, wherein the content of the stabilizing agent is 2–4%.

47. The PFOC emulsion of claim 46, wherein the physiologically acceptable aqueous-saline solution comprises NaCl, KCl, $MgCl_2$, $NaHCO_3$, $NaH_2PO_4$ and D-glucose.

48. The PFOC emulsion of claim 46, comprising:
   a main rapidly eliminable perfluorocarbon in the form of a mixture of cis- and trans-isomers of perfluorodecalin in an amount of 6 vol. %;
   admixtures of rapidly eliminable perfluorocarbons comprising a mixture of perfluoromethylindane, perfluoro-1-methyl-3-propylcyclohexane, trans-perfluoroindane, perfluoro-4-oxo-decalin, perfluorobutylcyclohexane, perfluoropropylcyclohexane, perfluoroethylcyclohexane, perfluorobutylcyclopentane, cisperfluoro-1-methyl-2-ethylcyclohexane in an amount of 0.7 vol. %;
   a main slowly eliminable perfluorinated tertiary amine in the form of a mixture of isomers of perfluoro-N-4-(methyl-cyclohexyl)piperidine in an amount of 2.3 vol. %;
   admixtures of perfluorinated tertiary amines, comprising a mixture of perfluoro-N-(4-methylcyclohexyl)-2-methylpyrrolidine, perfluoromethylbutyl-(4-methylcyclohexyl)-amine, cis- and trans-isomers of perfluoromethylpropyl-(4-methylcyclohexyl)-amine, a mixture of isomers of perfluoromethylpropyl-(methylcyclopentyl)-amine and perfluoro-N-(4-methylcyclohexyl)-1-methylpiperidine in a total amount of 1.0 vol. %;
   wherein
      the content of H-perfluoroalkanes is 0.02 vol. %; and
      the ratio of polyoxyethylene and polyoxypropylene blocks in the copolymer is 4:1 with the molecular mass of 8,000 Da.

49. The emulsion of claim 46, wherein the aqueous-saline solution comprises 102 mM of NaCl, 5.2 mM of KCl, 1.8 mM of $MgCl_2$, 7.7 mM of $NaHCO_3$, 1.65 mM of $NaH_2PO_4$, 11 mM of D-glucose, 5 mM of sodium pyruvate, 5 mM of sodium β-oxybutyrate, 5 mM of sodium succinate, 5 mM of sodium glutamate and 5 mM of taurine.

50. A method for treating vascular air-and-fat embolism comprising intravenously administering to a subject in need thereof a 5 ml/kg or lower dose of the emulsion of claim 1.

51. A method for treating obliterating vascular injuries of extremities comprising intravenously administering to a subject in need thereof a 5 ml/kg or lower dose of the emulsion of claim 1.

52. A method for accelerating lipophilic xenobiotic metabolism comprising intravenously administering to a subject in need thereof a 5 ml/kg or lower dose of the emulsion of claim 1.

53. A process for the preparation of an emulsion of perfluoroorganic compounds (PFOC), comprising mixing apyrogenic sterile components by passing a mixture of liquid perfluoroorganic compounds through an aqueous solution of a stabilizing agent and subsequent multiple homogenization of the resulting pro-emulsion in a two-circuit high-pressure homogenizer,
   wherein
      before mixing, the mixture of liquid perfluoroorganic compounds and the aqueous solution of the stabilizing agent are saturated with carbon dioxide gas, whereafter the aqueous solution of the stabilizing agent is heated at a temperature not over 75° C.,
      the mixture of liquid perfluoroorganic compounds is fed into a solution of the cooled stabilizing agent at least in two jets in the atmosphere of carbon dioxide gas, the pro-emulsion is stirred intensively with a simultaneous passing thereof through the first circuit of the homogenizer at a pressure of 300–450 $kg/cm^2$,
      the emulsion is subjected to multiple homogenization in the second circuit of the homogenizer at a pressure of 400–600 $kg/cm^2$, and
      the process of preparing the pro-emulsion and of the subsequent homogenization is carried out in the atmosphere of carbon dioxide gas.

54. The process of claim 53, wherein the solution of the stabilizing agent is heated at a temperature of 70° C. for 12 hours.

* * * * *